United States Patent
Nagashima et al.

(10) Patent No.: US 11,034,712 B2
(45) Date of Patent: Jun. 15, 2021

(54) METHOD FOR PRODUCING TRANSITION METAL-ISOCYANIDE COMPLEX

(71) Applicants: KYUSHU UNIVERSITY, NATIONAL UNIVERSITY CORPORATION, Fukuoka (JP); SHIN-ETSU CHEMICAL CO., LTD., Tokyo (JP)

(72) Inventors: Hideo Nagashima, Fukuoka (JP); Atsushi Sanagawa, Fukuoka (JP); Daisuke Noda, Annaka (JP); Koji Sakuta, Annaka (JP)

(73) Assignees: KYUSHU UNIVERSITY, NATIONAL UNIVERSITY CORPORATION, Fukuoka (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/489,520

(22) PCT Filed: Feb. 27, 2018

(86) PCT No.: PCT/JP2018/007216
§ 371 (c)(1),
(2) Date: Aug. 28, 2019

(87) PCT Pub. No.: WO2018/159599
PCT Pub. Date: Sep. 7, 2018

(65) Prior Publication Data
US 2020/0071347 A1  Mar. 5, 2020

(30) Foreign Application Priority Data
Feb. 28, 2017  (JP) .............................. JP2017-036985

(51) Int. Cl.
*C07F 15/06* (2006.01)
*C07C 291/10* (2006.01)
(Continued)

(52) U.S. Cl.
CPC ............ *C07F 15/06* (2013.01); *C07C 291/10* (2013.01); *C07F 11/00* (2013.01); *C07F 15/006* (2013.01);
(Continued)

(58) Field of Classification Search
None
See application file for complete search history.

(56) References Cited

U.S. PATENT DOCUMENTS

2005/0151278 A1  7/2005  Lefenfeld et al.

FOREIGN PATENT DOCUMENTS

JP  4885730 B2  2/2012
JP  5048503 B2  10/2012
(Continued)

OTHER PUBLICATIONS

Adams et al., "The Catalytic Activity of Transition Metal Complexes of Sterically Hindered Isocyanides," Journal of Molecular Catalysis, vol. 29, 1985, pp. 201-208.
(Continued)

*Primary Examiner* — Clinton A Brooks
(74) *Attorney, Agent, or Firm* — Birch, Stewart, Kolasch & Birch, LLP

(57) ABSTRACT

This method is for producing a transition metal complex represented by formula (2), the method comprising reacting a compound containing a transition metal selected from V, Cr, Mo, W, Fe, Ru, Co, Rh, Ni, Pd, and Pt with an isocyanide compound represented by formula (1) in the presence of an alkali metal supported by a solid substance which is insoluble in an organic solvent. This production method can
(Continued)

be used to easily and efficiently produce a transition metal complex that includes a predetermined transition metal having an oxidation number of 0 and that has the same or different isocyanide compounds, without using a compound harmful to the human body. (1): $(CN)_x$—$R^1$ {$R^1$ represents a mono- to tri-valent organic group having 1-30 carbon atoms, and x represents an integer of 1-3}. (2): $M^1{}_a(L)_b$ {$M^1$ represents V, Cr, Mo, W, Fe, Ru, Co, Rh, Ni, Pd, or Pt, and is a zero-valent transition metal, L represents an isocyanide compound represented by formula (1), $M^1$ and L may be the same or different from each other, "a" represents an integer of 1-8, and b represents an integer of 2-12}.

17 Claims, 7 Drawing Sheets

(51) Int. Cl.
    *C07F 11/00*         (2006.01)
    *C07F 15/00*         (2006.01)
    *C07F 15/02*         (2006.01)
    *C07F 15/04*         (2006.01)

(52) U.S. Cl.
    CPC ...... *C07F 15/0046* (2013.01); *C07F 15/0073* (2013.01); *C07F 15/0086* (2013.01); *C07F 15/02* (2013.01); *C07F 15/04* (2013.01)

(56) References Cited

FOREIGN PATENT DOCUMENTS

JP           5346986 B2     11/2013
JP           5385358 B2     1/2014
JP     2016-160487 A     9/2016

OTHER PUBLICATIONS

Albers et al., "Catalysed and Non-catalysed Reaction Between [Fe(CO)$_5$] and Isonitriles," J. Chem. Soc. Dalton Trans., Jan. 1, 1982, pp. 1069-1079.

Albers et al., "Metal Carbonyl Substitution Reactions catalysed by Transition Metal Complexes," J.C.S. Chem. Comm., Jan. 1, 1980, pp. 489-490.

Barker et al., "Synthesis and Reactions of Octakis(t-butyl isocyanide)dicobalt and Pentakis(t-butyl isocyanide)ruthenium; X-Ray Crystal and Molecular Structures of [Co$_2$(Bu$^t$NC)$_8$] and [Ru(Ph$_3$P)(Bu$^t$NC)$_4$]," J.Chem. Soc. Chem. Commun., 1977, pp. 256-259.

Barybin et al., "First Homoleptic Isocyanides of Niobium and Tantalum," J. Am. Chem. Soc., vol. 121, No. 39, 1999 (published on web Sep. 21, 1999), pp. 9237-9238.

Barybin et al., "First Paramagnetic Zerovalent Transition Metal Isocyanides. Syntheses, Structural Characterizations, and Magnetic Properties of Novel Low-Valent Isocynaide Complexes of Vanadium," J. Am. Chem. Soc., vol. 122, No. 19, 2000 (published on web Apr. 27, 2000), pp. 4678-4691.

Barybin et al., "Homoleptic Isocyanidemetalates of 4d- and 5d-Transition Metals: [Nb(CNXyl)$_6$]-, [Ta(CNXyl)$_6$]-, and Derivatives Thereof," J. Am. Chem. Soc., vol. 129, No. 5, 2007 (published on web Jan. 11, 2007), pp. 1141-1150.

Bassett et al., "Chemistry of Low-valent Metal Isocyanide Complexes. Part 1. Synthesis of Zerovalent Iron and Ruthenium Complexes. Crystal and Molecular Structures of Tetrakis(t-butyl isocyanide)(triphenylphosphine) ruthenium and Pentakis(t-butyl isocyanide)iron," J. Chem. Soc., Dalton Trans Jan. 1, 1979 pp. 1003-1011.

Chakraborty et al., "Functionalization of Potassium Graphite," Angew. Chem. Int. Ed., vol. 46, 2007, pp. 4486-4488.

Chalk et al., "Homogeneous Catalysis. IV. Some Reactions of Silicon Hydrides in the Presence of Cobalt Carbonyls," Journal of the American Chemical Society, vol. 89, No. 7, Mar. 29, 1967, pp. 1640-1647.

Christofides, "Xylyl Isocyanide Platinum and Palladium Complexes," Journal of Organometallic Chemistry, vol. 259, 1983, pp. 355-365.

Coco et al., "Insertion of Mercury into Iron-Halogen Bonds. X-Ray Structure of [(p-MeC$_6$H$_4$NC)$_5$Fe→HgI$_2$]," J. Chem. Soc. Dalton Trans., Jan. 1, 1991, pp. 2503-2509.

International Search Report for International Application No. PCT/JP2018/007216, dated May 29, 2018, with English translation.

Jones et al., "Preparation and Structural Examination of a Series of New, Low-Valent Iron Phosphine Isocyanide Complexes with Bent C-N-C Linkages," Inorg. Chem., vol. 26, No. 13, 1987, pp. 2120-2127.

Leach et al., "Synthesis and Stuctural Characterization of [Co{CN(2,6-C H$_{6\ 3}$ Me )$_2$ }$_4$ ]-, the First Transition Metal Isonitrilate," J. Am. Chem. Soc., vol. 116, No. 19, 1994 (abstract published in advance on May 1, 1994), pp. 8566-8574.

Lentz et al., "Transition metal complexes and cycloaddition products of pentafluorophenyl isocyanide," Journal of Fluorine Chemistry, vol. 89, 1998, pp. 73-81.

Lentz, "Homoleptische Trifluormethylisocyanid-Eisenkomplexe, Fe(CNCF3)5 and Fe2(CNCF3)9," Journal of Organometallic Chemistry, vol. 377, 1989, pp. 305-308, with English abstract.

Margulieux et al., "Isocyano Analogues of [Co(CO)$_4$]$^n$: A Tetraisocyanide of Cobalt Isolated in Three States of Charge," J. Am. Chem. Soc., vol. 132, No. 14, 2010 (published on web Mar. 21, 2010), pp. 5033-5035.

Mautz et al., "Reductive Activation of tripod Metal Compounds: Identification of Intermediates and Preparative Application," Eur. J. Inorg. Chem., 2008, pp. 1413-1422.

Minelli et al., "Multinuclear NMR Studies of Molybdenum and Tungsten Carbonyl Isocyanide Complexes," Inorg. Chem., vol. 28, No. 15, 1989, pp. 2954-2958.

Mitchener et al., "Photogeneration of Very Active Homogeneous Catalysts Using Laser Light Excitation of Iron Carbonyl Precursors," Journal of the American Chemical Society, vol. 103, No. 4, 1981, pp. 975-977.

Mokhtarzadeh et al., "Dinitrogen binding, P$_4$-activation and aza-Büchner ring expansions mediated by an isocyano analogue of the CpCo(CO)fragment," Dalton trans., vol. 45, Jul. 21, 2016, pp. 14561-14569.

Mokhtarzadeh et al., "Synthesis and Protonation of an Encumbered Iron Tetraisocyanide Dianion," Inorg. Chem., vol. 54, May 12, 2015, pp. 5579-5587.

Noda et al., "Non-Precious-Metal Catalytic Systems Involving Iron or Cobalt Carboxylates and Alkyl Isocyanides for Hydrosilylation of Alkenes with Hydrosiloxanes," Journal of the American Chemical Society, vol. 138, Jan. 13, 2016, pp. 2480-2483.

Otsuka et al., "Oxygen Complexes of Nickel and Palladium. Formation, Structure, and Reactivities," Journal of the American Chemical Society, vol. 91, No. 25, Dec. 3, 1969, pp. 6994-6999.

Reichel et al., "Photochemistry of Cobalt Carbonyl Complexes Having a Cobalt-Silicon Bond and Its Importance in Activation of Catalysis," Inorg. Chem., vol. 19, No. 12, 1980, pp. 3858-3860.

Ruiz et al., "A Homoleptic (Aryl Isocyanide)Iron(0) Dimer. X-ray Structure Determination of Nonakls(phenyl Isocyanide )diiron," Organometallics, vol. 11, No. 7, 1992, pp. 2734-2736.

Schroeder et al., "Pentacarbonyliron(0) Photocatalyzed Reactions of Trialkylsilanes with Alkenes," Journal of Organometallic Chemistry, vol. 128, 1977, pp. 345-358.

Sunada et al., "Combinatorial Approach to the Catalytic Hydrosilylation of Styrene Derivatives: Catalyst Systems Composed of Organoiron(0) or (II) Precursors and Isocyanides," Organometallics, vol. 34, Jun. 3, 2015, pp. 2896-2906.

Timms et al., "Reactions of Transition-metal Vapours with Cycloheptatriene and Cyclo-octatetraene," J.Chem. Soc., Dalton Trans., Jan. 1, 1976, pp. 2021-2025.

Written Opinion of the International Searching Authority for International Application No. PCT/JP2018/007216, dated May 29, 2018.

(56) References Cited

OTHER PUBLICATIONS

Yamamoto et al., "A Seven-Platinum Cluster Containing a Trigonal-Bipyramidal Unit as the Main Framework, Pt$_7$(2,6-Me$_2$C$_6$H$_3$NC)$_{12}$," Organometallics, vol. 2, No. 10, 1983, pp. 1377-1381.

Yamamoto et al., "Studies of the Interaction of Isocyanides with Transition-metal Complexes. XXVI. The Preparation of Octakis(aryl isocyanide)dirhodium," Bull. Chem. Soc. Jpn., vol. 57, No. 1, Jan. 1984, pp. 297-298.

Yamamoto et al., "Studies on the Interaction of Isocyanides with Transition Metal Complexes XXVII. Preparation of Zerovalent Isocyanide Complexes of Chromium, Molybdenum and Tungsten. The Crystal Structure of Hexakis(2,6-Xylyl Isocyanide) Molybdenum Containing Benzene as a Solvated Molecule," Journal of Organometallic Chemistry, vol. 282, 1985, pp. 191-200.

Yamamoto et al., "Synthesis and Reactions of Dicobalt Octaisocyanide[1,2]," Inorganic Chemistry, vol. 17, No. 11, 1978, pp. 3111-3114.

Yamamoto et al., "The Preparation and Chemistry of a Zerovalent Cobalt(0) Complex Containing Only Isocyanide Ligands," Journal of Organometallic Chemistry, vol. 137, 1977, pp. C31-C33.

Chiu et al., "t-Butyl Isocyanide Complexes of Rhenium(I), Chromium(O), Tungsten(O,I) and Platinum(II); X-Ray Crystal . . . Phosphine)Chlororhenium(I)", Polyhedron, vol. 1, No. 11-12, 1982, pp. 803-808.

Extended European Search Report dated Jul. 9, 2020 for Application No. 18761893.9.

METHOD FOR PRODUCING TRANSITION METAL-ISOCYANIDE COMPLEX

TECHNICAL FIELD

The present invention relates to a method for producing a transition metal-isocyanide complex.

BACKGROUND ART

An isocyanide or isonitrile compound (hereinafter, collectively referred to as an isocyanide compound) is a compound having an isocyano group formed of a triple bond of carbon and nitrogen; unlike a nitrile compound, the isocyanide compound has an unshared electron pair on carbon and has a substituent on nitrogen, and is known for having an electronic structure equal to a carbon monoxide ligand.

For this feature, from old times isocyanide compounds have been used as reaction intermediates of various nitrogen-containing compounds, and have been used as ligands of transition metal complexes similarly to carbon monoxide.

Examples in which isocyanide compounds are used as ligands of catalysts for hydrosilylation reaction are reported. Hydrosilylation reaction in which a Si—H functional compound is reacted to be added to a compound having a carbon-carbon double bond is a useful means for synthesizing an organic silicon compound, and is an industrially important synthesis reaction.

As the catalyst for hydrosilylation reaction, Pt, Pd and Rh compounds are known. Among others, Pt compounds as typified by Speier's catalyst and Karstedt's catalyst are most commonly used. As a catalyst for hydrosilylation reaction using an isocyanide compound, an example using a catalyst produced by adding an aryl isocyanide compound to a rhodium complex is reported (Non-Patent Document 1).

These days, hydrosilylation reaction catalysts using inexpensive iron or cobalt and having isocyanide compounds as ligands are reported. For example, a hydrosilylation reaction catalyst using bis(cyclooctatetraenyl)iron and an isocyanide compound as ligands is reported (Non-Patent Document 2). Also a hydrosilylation reaction catalyst using iron pivalate or cobalt pivalate and an isocyanide compound as ligands is reported (Non-Patent Document 3), and it is reported that an isocyanide compound is useful as a ligand of a catalyst for hydrosilylation reaction. However, all these examples are still insufficient in terms of catalytic activity, and the development of a catalyst having higher catalytic activity is desired.

As a common method for improving catalytic activity, a technique using a complex having a structure close to an active species of the reaction is known. Chalk-Harrod mechanism and modified Chalk-Harrod mechanism are known as reaction mechanisms of hydrosilylation reaction (Non-Patent Documents 4 to 7); a complex with an oxidation number of zero is close to a catalytic active species. That is, it is expected that catalytic activity will be improved when a zero-valent transition metal complex having an isocyanide compound as ligands is used as a catalyst.

Thus far, a zero-valent transition metal complex having an isocyanide compound as ligands has been synthesized by, for example, reacting together a halide salt, an acetate, or a hexafluorophosphate, an isocyanide compound, and sodium amalgam or potassium amalgam as a reducing agent (Non-Patent Documents 8 to 14); however, in this technique, highly toxic mercury is used, and a complex containing mercury like in Non-Patent Document 15 may be contained in the product depending on the reaction conditions.

Further, a method in which a zero-valent transition metal complex having carbon monoxide as ligands and an isocyanide compound are reacted together to perform synthesis is reported (Non-Patent Documents 10, and 16 to 20). However, while an aromatic isocyanide compound can create a state where all carbonyl ligands are substituted with isocyanide ligands, in an aliphatic isocyanide compound, it is difficult to create such a state, and highly toxic carbon monoxide is generated during the reaction.

In this respect, a method in which a precursor of a zero-valent transition metal complex having substitutable ligands other than carbon monoxide and an isocyanide compound are reacted together is reported (Non-Patent Documents 21 to 26); however, the precursor is unstable to air or water, and is hard to handle.

Also an example in which an ate-type (or ion-structured) transition metal complex having an isocyanide compound as ligands is used as a precursor of a complex is reported (Non-Patent Documents 27 and 28); however, also in this case, sodium amalgam containing mercury is used when synthesizing the ate-type transition metal complex, and there is a problem of high toxicity like in the technology mentioned above.

Further, a synthesis example in which potassium naphthalenide is used as a reducing agent is reported (Non-Patent Document 29); however, it is necessary to dispose of a large amount of naphthalene produced after reaction, and there is a problem with the purification of the complex.

On the other hand, these days, an alkali metal supported by a solid substance insoluble in an organic solvent as a reducing agent and a use example thereof are reported, and the ease of handling, the ease of reactivity and purification, or an improvement in safety is achieved; however, there is no example in which such a supported alkali metal is used for the synthesis of a zero-valent transition metal complex that is useful as a catalyst for hydrosilylation reaction and that has a transition metal and an isocyanide compound as ligands (Patent Documents 1 to 5, and Non-Patent Documents 30 and 31).

PRIOR ART DOCUMENTS

Patent Documents

Patent Document 1: JP 4885730
Patent Document 2: JP 5346986
Patent Document 3: JP 5385358
Patent Document 4: JP 5048503
Patent Document 5: JP-A 2016-160487

Non-Patent Documents

Non-Patent Document 1: J. M. Walters, et al., J. Molecular Catalysis, 1985, 29, 201
Non-Patent Document 2: H. Nagashima, et al., Organometallics, 2015, 34, 2896
Non-Patent Document 3: H. Nagashima, et al., J. Am. Chem. Soc., 2016, 138, 2480
Non-Patent Document 4: M. S. Wrighton, et al., J. Organomet. Chem., 1981, 103, 975
Non-Patent Document 5: M. S. Wrighton, et al., J. Am. Chem. Soc., 1977, 128, 345
Non-Patent Document 6: M. S. Wrighton, et al., Inorg. Chem., 1980, 19, 3858
Non-Patent Document 7: A. J. Chalk, et al., J. Am. Chem. Soc., 1967, 89, 1640

Non-Patent Document 8: F. G. A. Stone, et al., J. Chem. Soc., Dalton Trans., 1979, 1003

Non-Patent Document 9: M. Vivanco, et al., Organometallics, 1992, 11, 2734

Non-Patent Document 10: Y. Yamamoto, et al., Inorg. Chem., 1978, 17, 3111

Non-Patent Document 11: P. Woodward, et al., J. Chem. Soc., Chem. Commun., 1977, 256

Non-Patent Document 12: Y. Yamamoto, et al., J. Organomet. Chem., 1985, 282, 191

Non-Patent Document 13: Y. Yamamoto, et al., Bull. Chem. Soc. Jpn., 1984, 57, 297

Non-Patent Document 14: Y. Yamamoto, et al., Organometallics, 1983, 2, 1377

Non-Patent Document 15: P. Espinet, et al., J. Chem. Soc., Dalton Trans., 1991, 2503

Non-Patent Document 16: F. G. A. Stone, et al., J. Chem. Soc., Chem. Commun., 1980, 489

Non-Patent Document 17: N. J. Coville, et al., J. Chem. Soc., Dalton Trans., 1982, 1069

Non-Patent Document 18: Y. Yamamoto, et al., J. Organomet. Chem., 1977, 137, C31

Non-Patent Document 19: M. Minelli, et al., Inorg. Chem., 1989, 28, 2954

Non-Patent Document 20: D. Lentz, et al., J. Fluorine Chem., 1998, 89, 73

Non-Patent Document 21: D. Lentz, J. Organomet. Chem., 1989, 377, 305

Non-Patent Document 22: W. D. Jones, et al., Inorg. Chem., 1987, 26, 2120

Non-Patent Document 23: J. E. Ellis, et al., J. Am. Chem. Soc., 2000, 4678

Non-Patent Document 24: T. W. Turney, et al., J. Chem. Soc., Dalton Trans., 1976, 2021

Non-Patent Document 25: S. Otsuka, et al., J. Am. Chem. Soc., 1969, 91, 6994

Non-Patent Document 26: A. Christofides, et al., J. Organomet. Chem., 1983, 259, 355

Non-Patent Document 27: J. S. Figueroa, et al., Inorg. Chem., 2015, 54, 5579

Non-Patent Document 28: J. S. Figueroa, et al., J. Am. Chem. Soc., 2010, 132, 5033

Non-Patent Document 29: N. J. Cooper, et al., J. Am. Chem. Soc., 1994, 116, 8566

Non-Patent Document 30: W. E. Billups, et al., Angew. Chem. Int. Ed., 2007, 46, 4486

Non-Patent Document 31: J. E. Ellis, et al., J. Am. Chem. Soc., 2007, 129, 1141

SUMMARY OF INVENTION

Technical Problem

The present invention has been made in view of such circumstances, and an object of the present invention is to provide a method that, without using a compound harmful to human bodies, can easily and efficiently produce a transition metal complex formed of a prescribed transition metal that has an oxidation number of zero and that has identical or different isocyanide compounds.

Solution to Problem

The present inventors conducted extensive studies in order to achieve the object mentioned above; and have found out that reaction progresses under mild conditions by reacting together a compound containing a prescribed transition metal and a prescribed isocyanide compound in the presence of an alkali metal supported by a solid substance insoluble in an organic solvent, and have found out that, since the alkali metal supported by a solid substance is insoluble in an organic solvent, the supported alkali metal can be easily removed by a simple process of filtration, and consequently a transition metal-isocyanide complex can be produced efficiently and safely; thus, have completed the present invention.

The invention provides a transition metal-isocyanide complex and a method defined below.

1. A method for producing a transition metal-isocyanide complex represented by formula (2) below, the method including reacting together a compound containing a transition metal selected from V, Cr, Mo, W, Fe, Ru, Co, Rh, Ni, Pd, and Pt, and an isocyanide compound represented by formula (1) below in the presence of an alkali metal supported by a solid substance insoluble in an organic solvent, $$(CN)_x\text{—}R^1 \tag{1}$$

wherein $R^1$ represents a monovalent to trivalent organic group that has 1 to 30 carbon atoms and is optionally substituted with a halogen atom and in which one or more atoms selected from oxygen, nitrogen, sulfur, and silicon are optionally interposed, and x represents an integer of 1 to 3, $$M^1_a(L)_b \tag{2}$$

wherein $M^1$ represents V, Cr, Mo, W, Fe, Ru, Co, Rh, Ni, Pd, or Pt with an oxidation number of zero, L represents an isocyanide compound represented by the formula (1), $M^1$ may be the same or different, and L may be the same or different, "a" represents an integer of 1 to 8, and "b" represents an integer of 2 to 12.

2. The method for producing a transition metal-isocyanide complex according to 1, wherein the compound containing a transition metal is at least one selected from a transition metal oxide, a transition metal acid or a salt thereof, and a halide salt, an oxyacid salt, a carboxylate, a sulfonate, an alkoxide salt, a β-diketonate, an amide salt, a tetrafluoroborate, or a hexafluorophosphate of the transition metal.

3. The method for producing a transition metal-isocyanide complex according to 1 or 2, wherein the solid substance insoluble in an organic solvent is at least one selected from a carbon material, a silicon compound, a metal oxide, and a polymer compound.

4. The method for producing a transition metal-isocyanide complex according to any one of 1 to 3, wherein, in the formula (2), when a is 1, b is an integer of 2 to 6, when a is 2, b is an integer of 4 to 10, and when a is an integer of 3 to 8, b is an integer of 4 to 12.

5. The method for producing a transition metal-isocyanide complex according to any one of 1 to 4, wherein, in the formula (1), x is 1.

6. The method for producing a transition metal-isocyanide complex according to any one of 1 to 5, wherein, in the formula (2), $M^1$ is Cr, Mo, W, Fe, Ru, Co, Rh, Ni, Pd, or Pt.

7. The method for producing a transition metal-isocyanide complex according to any one of 1 to 6, wherein, in the formula (2), when a is 1, b is an integer of 2 to 6, when a is 2, b is an integer of 4, or 8 to 10, and when a is an integer of 3 to 8, b is 4, 6, 7, 10, or 12.

8. The method for producing a transition metal-isocyanide complex according to any one of 1 to 7, wherein $M^1$ in the formula (2) is Fe, Co, Rh, Ni, Pd, or Pt.

9. The method for producing a transition metal-isocyanide complex according to any one of 1 to 7, wherein the compound containing a transition metal is a transition metal salt represented by formula (3) below, $$M^2X_c \quad (3)$$

wherein $M^2$ represents Cr, Mo, W, Fe, Ru, Co, Rh, Ni, Pd, or Pt, X represents a halogen atom or a group represented by formula (4) below each of which is possibly the same as or different from another one, and c represents an integer of 1 to 6, $$-OC(O)R^2 \quad (4)$$

wherein $R^2$ represents a monovalent organic group that has 1 to 30 carbon atoms and is optionally substituted with a halogen atom and in which one or more atoms selected from oxygen, nitrogen, sulfur, and silicon are optionally interposed.

10. The method for producing a transition metal-isocyanide complex according to 9, wherein, in the formula (3), $M^2$ is Fe, Co, Rh, Ni, Pd, or Pt.

11. The method for producing a transition metal-isocyanide complex according to 9 or 10, wherein $R^2$ in the formula (4) is a monovalent hydrocarbon group having 1 to 30 carbon atoms.

12. The method for producing a transition metal-isocyanide complex according to 11, wherein $R^2$ in the formula (4) is a methyl group.

13. The method for producing a transition metal-isocyanide complex according to any one of 9 to 12, wherein X in the formula (3) is at least one selected from chlorine, bromine, and iodine.

14. The method for producing a transition metal-isocyanide complex according to any one of 1 to 13, wherein $R^1$ in the formula (1) is a monovalent hydrocarbon group having 1 to 30 carbon atoms.

15. The method for producing a transition metal-isocyanide complex according to any one of 1 to 14, wherein $R^1$ in the formula (1) is at least one hydrocarbon group selected from an alkyl group having 1 to 20 carbon atoms, a cycloalkyl group having 5 to 20 carbon atoms, an aryl group having 6 to 30 carbon atoms, and an alkylaryl group having 7 to 30 carbon atoms.

16. The method for producing a transition metal-isocyanide complex according to 15, wherein $R^1$ in the formula (1) is at least one hydrocarbon group selected from a t-butyl group, a 1-adamantyl group, a mesityl group, a phenyl group, a 2,6-dimethylphenyl group, and a 2,6-diisopropylphenyl group.

17. The method for producing a transition metal-isocyanide complex according to any one of 1 to 16, wherein the solid substance insoluble in an organic solvent is at least one selected from graphite and silica gel.

18. The method for producing a transition metal-isocyanide complex according to any one of 1 to 17, wherein the alkali metal is at least one selected from sodium, potassium, and sodium-potassium alloy.

Advantageous Effects of Invention

A method for producing a transition metal-isocyanide complex of the present invention does not release mercury or carbon monoxide harmful to human bodies and furthermore does not need to use a precursor unstable to air or water, and is therefore safe; and can remove an alkali metal supported by a solid substance insoluble in an organic solvent by a simple process of filtration; thus, the method is an easy and efficient method.

Further, in the production method of the present invention, the risk during the production of a transition metal complex can be minimized by using an alkali metal supported by a solid substance insoluble in an organic solvent, in which risks due to water sensitivity and high oxygen reactivity, which are peculiar to alkali metals, have been reduced, and very high usefulness is provided.

DESCRIPTION OF EMBODIMENTS

Figure 1:
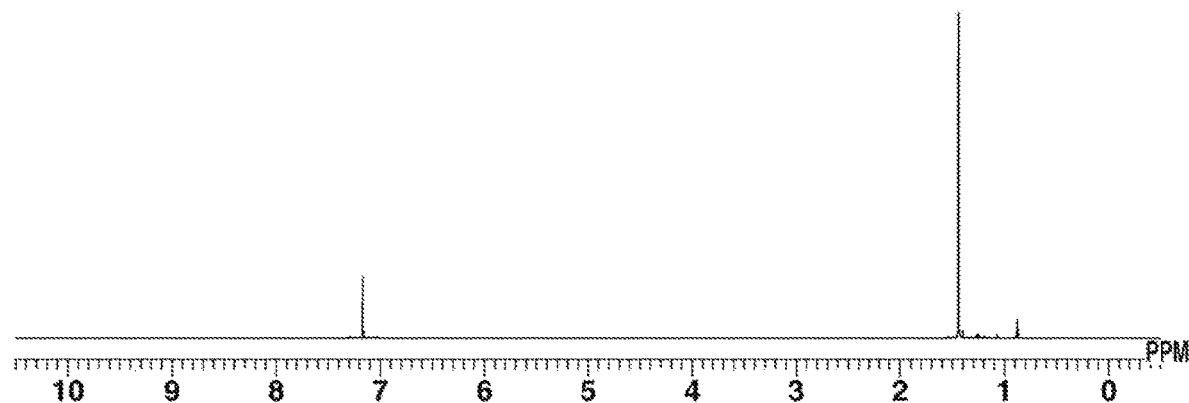
FIG. 1 is $^1$H-NMR spectrum diagram of $Co_2(CN^tBu)_8$ obtained in Example 1.

Below the invention is described in more detail.

A method for producing a transition metal-isocyanide complex according to the present invention reacts together a compound containing a transition metal and an isocyanide compound represented by formula (1) in the presence of an alkali metal supported by a solid substance insoluble in an organic solvent.

$$(CN)_x-R^1 \quad (1)$$

The transition metal used in the present invention is V, Cr, Mo, W, Fe, Ru, Co, Rh, Ni, Pd, or Pt, preferably Cr, Mo, W, Fe, Ru, Co, Rh, Ni, Pd, or Pt, and more preferably Fe, Co, Rh, Ni, Pd, or Pt.

The compound containing any of these transition metals is not particularly limited as long as it can be reduced by being reacted with an alkali metal supported by a solid substance insoluble in an organic solvent, and examples include transition metal oxides; transition metal acids such as chloroplatinic acid and chloroauric acid, or salts thereof; transition metal oxyacid salts such as sulfates, carbonates, and phosphates; transition metal halide salts such as fluorides, chlorides, bromide salts, and iodides; transition metal alkoxide salts such as methoxides, ethoxides, and isopropoxides; transition metal carboxylates such as acetates, pivalates, and 2-ethylhexanoates; transition metal β-diketonates such as acetylacetonates; transition metal sulfonates such as p-toluenesulfonates and trifluoromethanesulfonates; transition metal amide salts such as bis(trimethylsilyl)amides;

transition metal tetrafluoroborates; transition metal hexafluorophosphates; and the like; the compound is preferably a transition metal salt represented by formula (3) below.

$$M^2X_c \quad (3)$$

In formula (3), $M^2$ represents Cr, Mo, W, Fe, Ru, Co, Rh, Ni, Pd, or Pt, X represents a halogen atom or a group represented by formula (4) below, and c represents a number that changes in accordance with the oxidation number of the transition metal and represents an integer of 1 to 6.

$$-OC(O)R^2 \quad (4)$$

In formula (4), $R^2$ represents a monovalent organic group that has 1 to 30 carbon atoms and is optionally substituted with a halogen atom and in which one or more atoms selected from oxygen, nitrogen, sulfur, and silicon are optionally interposed.

Specific examples of the halogen atom include fluorine, chlorine, bromine, and iodine.

The monovalent to trivalent organic group having 1 to 30 carbon atoms is not particularly limited, but is preferably a monovalent to trivalent hydrocarbon group having 1 to 30 carbon atoms.

Examples of monovalent hydrocarbon groups include alkyl, alkenyl, alkynyl, aryl, alkyl aryl, and aralkyl groups.

The alkyl groups may be straight, branched or cyclic, is preferably 1 to 20, more preferably 1 to 10 alkyl group. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, 2-ethylhexyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, cyclononyl, norbornyl, and adamantyl.

The alkenyl group is preferably an alkenyl group having 2 to 20 carbon atoms, and examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl, and n-1-eicosenyl.

The alkynyl group is preferably an alkynyl group having 2 to 20 carbon atoms, and examples include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl, and n-1-eicosynyl.

The aryl or alkylaryl group is preferably an aryl group having 6 to 20 carbon atoms or an alkylaryl group having 7 to 20 carbon atoms, and specific examples include phenyl, 1-naphthyl, 2-naphthyl, anthryl, phenanthryl, o-biphenylyl, m-biphenylyl, p-biphenylyl, tolyl, 2,6-dimethylphenyl, 2,6-diisopropylphenyl, a mesityl group, and the like.

The aralkyl group is an arylalkyl group preferably having 7 to 30 carbon atoms and more preferably having 7 to 20 carbon atoms, and specific examples include benzyl, phenylethyl, phenylpropyl, naphthylmethyl, naphthylethyl, a naphthylpropyl group, and the like.

Suitable divalent hydrocarbon groups include alkylene, arylene and aralkylene groups.

The alkylene groups may be straight, branched or cyclic ones, preferably alkylene groups having 1 to 20 carbon atoms. Examples include straight or branched alkylene groups such as methylene, ethylene, propylene, trimethylene, n-butylene, isobutylene, s-butylene, n-octylene, 2-ethylhexylene, n-decylene, n-undecylene, n-dodecylene, n-tridecylene, n-tetradecylene, n-pentadecylene, n-hexadecylene, n-heptadecylene, n-octadecylene, n-nonadecylene, and n-eicosanylene; and cycloalkylene groups such as 1,4-cyclohexylene.

Examples of the arylene group include o-phenylene, m-phenylene, p-phenylene, 1,2-naphthylene, 1,8-naphthylene, 2,3-naphthylene, and 4,4'-biphenylene.

Examples of the aralkylene group include $-(CH_2)_y-Ar-$ wherein Ar is an arylene group having 6 to 20 carbon atoms and y is an integer of 1 to 10, $-Ar-(CH_2)_y-$ wherein Ar and y are as defined above, and $-(CH_2)_y-Ar-(CH_2)_y-$ wherein Ar is as defined above and y is each independently as defined above.

Specific examples of the trivalent hydrocarbon group include those represented by the following formulae, but are not limited to these.

[Chem. 1]

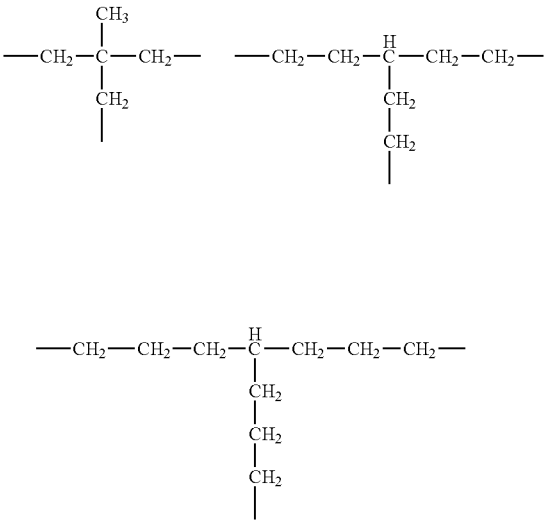

Specific examples of other organic groups in $R^2$ above include alkoxy groups such as a methoxy group, an ethoxy group, a propoxy group, and an isopropoxy group; aryloxy groups such as a phenoxy group; alkyl halide groups such as a trifluoromethyl group; alkylamino groups such as a dimethylamino group; ester groups such as a methyl ester and an ethyl ester; a nitro group; a nitrile group; alkyl- or arylsilyl groups such as a trimethylsilyl group and a phenyldimethylsilyl group; alkoxysilyl groups such as a trimethoxysilyl group, a triethoxysilyl group, a dimethoxymethylsilyl group, and a diethoxymethylsilyl group; nitrogen-containing heterocycle-containing groups such as a pyridyl group; sulfur-containing heterocycle-containing groups such as a thienyl group; and the like.

One or more atoms selected from oxygen, nitrogen, silicon, sulfur, and phosphorus may be interposed in each of the organic groups described above, and each of the organic groups described above may be substituted with a halogen atom.

Among these, as $R^2$, alkyl groups or cycloalkyl groups such as methyl, ethyl, n-butyl, t-butyl, n-hexyl, n-octyl, 2-ethylhexyl, stearyl, and a cyclohexyl group, and aryl groups such as a phenyl group are preferable, and a methyl group is more preferable.

Specific examples of the compound containing a transition metal that can be used in the present invention are as follows.

The iron salt includes iron halides such as $FeCl_2$, $FeBr_2$, $FeCl_3$, $FeBr_3$, and $FeI_3$; iron carboxylates such as $Fe(OAc)_2$, $Fe(stearate)_2$, and $Fe(stearate)_3$; and the like.

The cobalt salt includes cobalt halides such as $CoCl_2$, $CoBr_2$, and $CoI_2$; cobalt carboxylates such as $Co(OAc)_2$, $Co(benzoate)_2$, $Co(2\text{-ethylhexanoate})_2$, and $Co(stearate)_2$; and the like.

The nickel salt includes nickel halides such as $NiCl_2$, $NiBr_2$, and $NiI_2$; nickel carboxylates such as $Ni(OAc)_2$; and the like.

As the ruthenium salt, ruthenium halides such as $RuCl_2$ and $RuCl_3$, and the like are given.

As the rhodium salt, rhodium halides such as chloro(1,5-cyclooctadiene)rhodium (dimer) and $RhCl_3$; rhodium carboxylates such as $Rh_2(OAc)_4$; and the like are given.

As the palladium salt, palladium halides such as $PdCl_2$, $PdBr_2$, and $PdI_2$; palladium carboxylates such as $Pd(OAc)_2$; and the like are given.

As the chromium salt, chromium halides such as $CrCl_2$, $CrCl_3$, and $CrBr_3$; chromium carboxylates such as $Cr(OAc)_2$ and $Cr(OAc)_3$; and the like are given.

As the molybdenum salt, molybdenum halides such as $MoCl_3$ and $MoCl_5$; molybdenum carboxylates such as $Mo_2(OAc)_4$; and the like are given.

As the tungsten salt, tungsten halides such as $WCl_6$ and the like are given.

As the vanadium salt, vanadium halides such as $VCl_2$, $VCl_3$, $VBr_3$, and $VI_3$, and the like are given.

As the platinum salt, platinum halides such as $PtCl_2$ and $PtCl_3$; chloroplatinic acids such as $H_2PtCl_6$; chloroplatinates such as $K_2PtCl_6$; and the like are given.

In particular, as the compound containing a transition metal in the present invention, halides such as chlorides, bromides, and iodides; and carboxylates such as acetates are preferable, and halides such as chlorides, bromides, and iodides are more preferable, in terms of reactivity with a reducing agent.

In formula (3) above, a solvent or the like may be coordinated to $M^2$. Examples of the solvent or the like include water; ammonia; amines such as ethyleneimine, N,N-tetramethylethylenediamine, and pyridine; ethers such as dimethoxyethane, diglyme, and tetrahydrofuran; nitriles such as acetonitrile and benzonitrile; amides such as N,N-dimethylformamide, N,N-dimethylacetamide, and N-methylpyrrolidone; olefins such as ethylene, 1,3-butadiene, 1,3-cyclohexadiene, cyclooctene, 1,5-cyclooctadiene, and norbornadiene; aromatic hydrocarbons such as benzene, toluene, and p-cymene; and the like.

On the other hand, in formula (1) above, $R^1$ represents a monovalent to trivalent organic group that has 1 to 30 carbon atoms and may be substituted with a halogen atom and in which one or more atoms selected from oxygen, nitrogen, sulfur, and silicon may be interposed, and x represents an integer of 1 to 3.

As the monovalent to trivalent organic group having 1 to 30 carbon atoms, similar groups to those given as examples in the above are given; among them, a t-butyl group, a 1-adamantyl group, a mesityl group, a phenyl group, a 2,6-dimethylphenyl group, and a 2,6-diisopropylphenyl group are preferable as $R^1$.

x in formula (1) above represents an integer of 1 to 3, and is preferably 1 or 2 and more preferably 1.

The isocyanide compound represented by formula (1) above may be obtained as a commercially available product, or may be synthesized by a known method. For example, it may be obtained by a method in which a formylated product is obtained from an amine compound and formic acid, and subsequently the formylated product is reacted with phosphoryl chloride in the presence of an organic amine to be turned into an isocyanide (Synthesis Method 1; see Organometallics, 2004, 23, 3976-3981); as a method for obtaining a formylated product under mild conditions, a formylated product can be obtained by forming acetic formic anhydride from acetic anhydride and formic acid, and reacting the acetic formic anhydride with an amine compound (Synthesis Method 2; see Org. Synth., 2013, 90, 358-366). The obtained formylated product can be turned into an isocyanide by the method described in Synthesis Method 1, which is the same as above.

The synthesis can be made also by a method in which an amine compound and dichlorocarbene are reacted together to produce an isocyanide, which is a method not involving formylation (Synthesis Method 3; see Tetrahedron Letters, 1972, 17, 1637-1640).

Examples of the isocyanide compound include alkyl isocyanides such as methyl isocyanide, ethyl isocyanide, n-propyl isocyanide, cyclopropyl isocyanide, n-butyl isocyanide, isobutyl isocyanide, sec-butyl isocyanide, t-butyl isocyanide, n-pentyl isocyanide, isopentyl isocyanide, neopentyl isocyanide, n-hexyl isocyanide, cyclohexyl isocyanide, cycloheptyl isocyanide, 1,1-dimethylhexyl isocyanide, 1-adamantyl isocyanide, and 2-adamantyl isocyanide; aryl isocyanides such as phenyl isocyanide, 2-methylphenyl isocyanide, 4-methylphenyl isocyanide, 2,4-dimethylphenyl isocyanide, 2,5-dimethylphenyl isocyanide, 2,6-dimethylphenyl isocyanide, 2,4,6-trimethylphenyl isocyanide, 2,4,6-tri-t-butylphenyl isocyanide, 2,6-diisopropylphenyl isocyanide, 1-naphthyl isocyanide, 2-naphthyl isocyanide, 2-methyl-1-naphthyl isocyanide; aralkyl isocyanides such as benzyl isocyanide and phenylethyl isocyanide.

Examples of the diisocyanide compound include 1,2-diisocyanoethane, 1,3-diisocyanopropane, 1,4-diisocyanobutane, 1,5-diisocyanopentane, 1,6-diisocyanohexane, 1,8-diisocyanooctane, 1,12-diisocyanododecane, 1,2-diisocyanocyclohexane, 1,3-diisocyanocyclohexane, 1,4-diisocyanocyclohexane, 1,3-diisocyano-2,2-dimethylpropane, 2,5-diisocyano-2,5-dimethylhexane, 1,2-bis(diisocyanoethoxy)ethane, 1,2-diisocyanobenzene, 1,3-diisocyanobenzene, 1,4-diisocyanobenzene, 1,1'-methylenebis(4-isocyanobenzene), 1,1'-oxybis(4-isocyanobenzene), 3-(isocyanomethyl)benzyl isocyanide, 1,2-bis(2-isocyanophenoxy)ethane, bis(2-isocyanophenyl)phenyl phosphonate, bis(2-isocyanophenyl) isophthalate, bis(2-isocyanophenyl) succinate.

Examples of the triisocyanide compound include 1,3-diisocyano-2-(isocyanomethyl)-2-methylpropane, 1,5-diisocyano-3-(2-isocyanoethyl)pentane, 1,7-diisocyano-4-(3-isocyanopropyl)heptane, and 3-isocyano-N,N'-bis(3-isocyanopropyl)propane-1-amine.

A transition metal-isocyanide complex of the present invention obtained by reacting together the compound containing a transition metal described above and the isocyanide compound represented by formula (1) above is represented by formula (2).

$$M^1{}_a(L)_b \qquad (2)$$

In formula (2), $M^1$ represents V, Cr, Mo, W, Fe, Ru, Co, Rh, Ni, Pd, or Pt with an oxidation number of zero; and is preferably Cr, Mo, W, Fe, Ru, Co, Rh, Ni, Pd, or Pt, and more preferably Fe, Co, Rh, Ni, Pd, or Pt. When there are a plurality of $M^1$s, they may be the same or different.

L represents the isocyanide compound represented by formula (1) above; when there are a plurality of L's, they may be the same or different.

"a" represents an integer of 1 to 8, and "b" represents an integer of 2 to 12; from the viewpoints of the stability of the complex and catalytic activity, it is preferable that, when a is 1, b be an integer of 2 to 6; when a is 2, b be an integer of 4 to 10; when a is an integer of 3 to 8, b be an integer of 4 to 12; it is more preferable that, when a is 1, b be 2 to 6; when a is 2, b be an integer of 4, or 8 to 10; when a is an integer of 3 to 8, b be 6, 7, 10, or 12.

In formula (2), L may be partially substituted with a known two-electron donating ligand, and a solvent or the like may be coordinated to L.

The two-electron donating ligand refers to a neutral compound having an unpaired electron; and is not particularly limited as long as it is a ligand other than a carbonyl ligand, and may be a nitrogen molecule, an ether compound, an amine compound, a phosphine compound, a phosphite compound, a sulfide compound, or the like; in view of the stability of the compound, it is preferable that all L's be isocyanide compound ligands.

As described above, in the present invention, the compound containing a transition metal mentioned above and the isocyanide compound represented by formula (1) above are reacted together in the presence of an alkali metal supported by a solid substance insoluble in an organic solvent.

Here, the solid substance insoluble in an organic solvent is not particularly limited as long as it is a solid substance insoluble in an organic solvent used for reaction; examples include carbon materials such as activated carbon, graphite, carbon nanofibers, and carbon nanotubes; silicon compounds such as silicon; metal oxides such as zeolite, zinc oxide, ceria, silica gel, alumina, and titanium oxide; polymer compounds such as polystyrene; and the like.

Specific examples of the alkali metal supported by a solid substance mentioned above include sodium, potassium, sodium-potassium alloy, and the like.

The alkali metal supported by a solid substance insoluble in an organic solvent mentioned above is not particularly limited, and may be selected for use from conventionally known ones like those described in Patent Documents 1 to 5 and Non-Patent Documents 25 and 26 above, and the like, as appropriate; examples include sodium, potassium, or sodium-potassium alloy supported by silica, alumina, graphite, titanium oxide, zeolite, zinc oxide, cerium oxide, or polystyrene; among these, potassium-carrying graphite (hereinafter, abbreviated as $KC_8$) is preferable from the viewpoint of reactivity, and sodium-carrying silica gel (Stage 1 or 2) is preferable in terms of low risk of ignitability etc. from the viewpoint of safety.

These alkali metals supported by a solid substance insoluble in an organic solvent may be obtained as commercially available products; as such commercially available products, $KC_8$ (manufactured by Strem Chemicals, Inc.), Na silica gel (manufactured by Aldrich Corporation, Stage I), Na silica gel (manufactured by Aldrich Corporation, Stage II), $NaK_2$ silica gel (manufactured by Aldrich Corporation, Stage I), and the like are given.

In the present invention, reaction conditions when producing a transition metal-isocyanide complex are not particularly limited.

The reaction temperature is usually approximately 10 to 100° C., and preferably 20 to 80° C.; the period of reaction is approximately 1 to 48 hours.

The reaction may be performed without a solvent, or may use an organic solvent in view of the control of the heat of reaction and the implementation of a post-treatment process after reaction.

As an organic solvent, for example, aliphatic hydrocarbons such as pentane, hexane, heptane, octane, and cyclohexane; ethers such as diethyl ether, diisopropyl ether, dibutyl ether, cyclopentyl methyl ether, tetrahydrofuran, and 1,4-dioxane; aromatic hydrocarbons such as benzene, toluene, xylenes, and mesitylene; and the like can be used.

The concentration of the reaction solution is not particularly limited, but the molar concentration (M) of the compound containing a transition metal is preferably 0.01 to 10 M and more preferably 0.01 to 2 M in view of the reactivity of the alkali metal supported by a solid substance insoluble in an organic solvent and the control of the heat of reaction.

In the production of the transition metal-isocyanide complex of the present invention, the molar ratio of the isocyanide compound to the compound containing a transition metal is not particularly limited, but is preferably 2 to 20 equivalents, and more preferably 2 to 10 equivalents.

Further, in the production of the transition metal-isocyanide complex of the present invention, the molar ratio of the alkali metal supported by a solid substance insoluble in an organic solvent to the compound containing a transition metal is not particularly limited, but is preferably 2 to 20 equivalents, and more preferably 2 to 8 equivalents.

As the post-treatment process after reaction, the reducing agent may be removed by filtration using a glass filter, filter paper, or the like, and the organic solvent may be distilled off by heating and/or pressure reduction.

The resulting compound may be used as it is, or may be purified by a known method. For example, the resulting compound may be cleaned with a solvent that the compound is insoluble or hardly soluble in, and may then be dried for use; alternatively, the resulting compound may be purified by reprecipitation or recrystallization by dissolving the compound in a good solvent and then performing cooling in this state, or by dissolving the compound in a good solvent and then adding a poor solvent that is diffusible in the good solvent.

EXAMPLES

Examples are given below by way of illustration and not by way of limitation.

All solvents were deoxygenated and dehydrated by well-known methods before they were used in the preparation of the compound containing a transition metal.

The compound containing a transition metal obtained was stored in a nitrogen gas atmosphere at 25° C. until they were used in reaction.

Hydrosilylation reaction and solvent purification of an alkene were always carried out in an inert gas atmosphere. The solvents and other ingredients were purified, dried and deoxygenated by well-known methods before they were used in various reactions.

The measurement of $^1$H-NMR was performed using JNM-ECA600 and JNM-LA400 manufactured by JEOL Ltd, and IR measurement was performed using FT/IR-550 manufactured by JASCO Corporation.

In the chemical structure formulae shown below, hydrogen atoms are omitted in accordance with common expression. $^t$Bu represents a t-butyl group, Ad an adamantyl group, and Mes a mesityl group.

[Example 1] Synthesis of Cobalt Isocyanide Complex $Co_2(CN^tBu)_8$ Using Cobalt Iodide and $KC_8$ Cobalt iodide (0.31 g, 1.0 mmol), tetrahydrofuran (hereinafter, abbreviated as THF) (15 mL), t-butyl isocyanide (0.33 g, 4.0 mmol), and $KC_8$ (manufactured by Strem Chemicals, Inc., 0.27 g, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 40 mL), and the insoluble matter was removed by celite filtration. The filtrate was cooled to −35° C. to perform recrystallization; thus, $Co_2(CN^tBu)_8$ was obtained (0.24 g, yield: 61%). $^1$H-NMR spectrum of the resulting complex is shown in FIG. 1.

$^1$H-NMR (600 MHz, $C_6D_6$) δ: 1.44 (s, 72H).
IR (ATR): ν=1666 (CN (bridge)), 2093, 1977, 1942 (CN (terminal)) $cm^{-1}$
Anal. Calcd. for $C_{40}H_{72}N_8Co_2$:
  C, 61.36; H, 9.27; N, 14.31 Found: C, 61.06; H, 9.52; N, 14.05.

[Example 2] Synthesis of Cobalt Isocyanide Complex $Co_2(CN^tBu)_8$ Using Cobalt Bromide and $KC_8$ Cobalt bromide (22 mg, 0.10 mmol), THF (3 mL), t-butyl isocyanide (33 mg, 0.40 mmol), and $KC_8$ (manufactured by Strem Chemicals, Inc., 27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Co_2(CN^tBu)_8$ was obtained (27 mg, yield: 70%).

[Example 3] Synthesis of Cobalt Isocyanide Complex $Co_2(CN^tBu)_8$ Using Cobalt Chloride and $KC_8$ Cobalt chloride (13 mg, 0.10 mmol), THF (3 mL), t-butyl isocyanide (33 mg, 0.40 mmol), and $KC_8$ (27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, cobalt isocyanide complex $Co_2(CN^tBu)_8$ was obtained (27 mg, yield: 70%).

[Example 4] Synthesis of Cobalt Isocyanide Complex $Co_2(CN^tBu)_8$ Using Cobalt Acetate and $KC_8$ Cobalt acetate (18 mg, 0.10 mmol), THF (3 mL), t-butyl isocyanide (33 mg, 0.40 mmol), and $KC_8$ (manufactured by Strem Chemicals, Inc., 27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Co_2(CN^tBu)_8$ was obtained (4 mg, yield: 10%).

Figure 2:
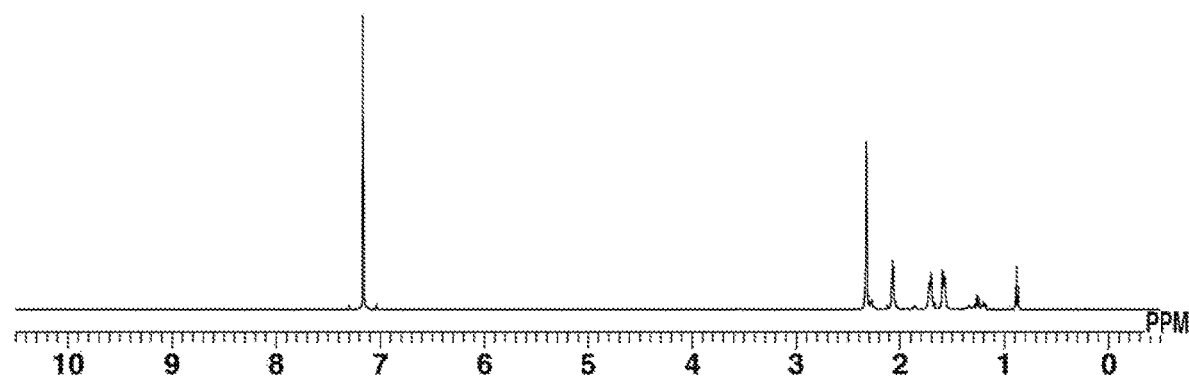
FIG. 2 is $^1$H-NMR spectrum diagram of $Co_2(CNAd)_8$ obtained in Example 5.

[Example 5] Synthesis of Cobalt Isocyanide Complex $Co_2(CNAd)_8$ Using Cobalt Iodide and $KC_8$ Cobalt iodide (0.31 g, 1.0 mmol), adamantyl isocyanide (0.65 g, 4.0 mmol), THF (15 mL), and $KC_8$ (manufactured by Strem Chemicals, Inc., 0.27 g, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in toluene (approximately 20 mL), and celite filtration was performed again. The solvent of the filtrate was distilled under reduced pressure, and then the dried substance was washed with a small amount of benzene (approximately 3 mL); thus, $Co_2(CNAd)_8$ was obtained (0.33 g, 47%). $^1$H-NMR spectrum of the resulting complex is shown in FIG. 2.

$^1$H-NMR (396 MHz, $C_6D_6$) δ:
  2.32 (s, 48H), 2.06 (s, 24H), 1.71 (d, J=10.3, 24H), 1.58 (d, J=10.3, 24H).
IR (ATR): ν=1647 (CN (bridge)), 2101, 2000, 1954 (CN (terminal)) $cm^{-1}$
Anal. Calcd. for $Ca_{88}H_{120}N_8Co_2$:
  C, 75.08; H, 8.59; N, 7.96 Found: C, 75.16; H, 8.62; N, 7.46.

Figure 3:
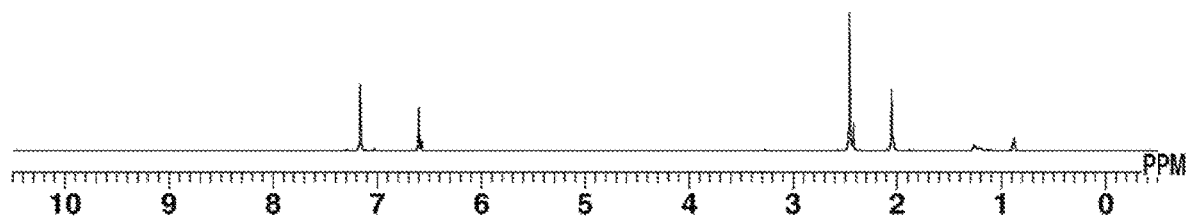
FIG. 3 is $^1$H-NMR spectrum diagram of $Co_2(CNMes)_8$ obtained in Example 6.

[Example 6] Synthesis of Cobalt Isocyanide Complex $Co_2(CNMes)_8$ Using Cobalt Iodide and $KC_8$ Cobalt iodide (13 mg, 0.10 mmol), mesityl isocyanide (58 mg, 0.40 mmol), THF (3 mL), and $KC_8$ (manufactured by Strem Chemicals, Inc., 27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in toluene (approximately 3 mL), and the insoluble matter was removed by celite filtration. Pentane (approximately 3 mL) was slowly added from above the filtrate to perform recrystallization; thus, a cobalt isocyanide complex of $Co_2$ $(CNMes)_8$ was obtained (42 mg, yield: 66%). $^1$H-NMR spectrum of the resulting complex is shown in FIG. 3.

$^1$H-NMR (396 MHz, $C_6D_6$) δ:
  6.60 (s, 12H), 6.58 (s, 4H), 2.46 (s, 36H), 2.42 (s, 12H), 2.05 (s, 18H), 2.03 (s, 6H).
IR (ATR): ν=1669 (CN (bridge)), 2063, 2026, 1954 (CN (terminal)) $cm^{-1}$
Anal. Calcd. for $C_{80}H_{88}N_8Co_2$:
  C, 75.10; H, 6.93; N, 8.60 Found: C, 75.21; H, 6.90; N, 8.60.

[Example 7] Synthesis of Cobalt Isocyanide Complex $Co_2(CN^tBu)_8$ Using Cobalt Iodide and Na Silica Gel (Stage I)

Cobalt iodide (0.31 g, 1.0 mmol), THF (15 mL), t-butyl isocyanide (0.33 g, 4.0 mmol), and Na silica gel (manufactured by Aldrich Corporation, Stage I, 0.34 g, 5.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 40 mL), and the insoluble matter was removed by celite filtration. The filtrate was cooled to −35° C. to perform recrystallization; thus, $Co_2(CN^tBu)_8$ was obtained (0.19 g, yield: 48%).

[Example 8] Synthesis of Cobalt Isocyanide Complex $Co_2(CN^tBu)_8$ Using Cobalt Iodide and Na Silica Gel (Stage II)

Cobalt iodide (0.31 g, 1.0 mmol), THF (15 mL), t-butyl isocyanide (0.33 g, 4.0 mmol), and Na silica gel (manufactured by Aldrich Corporation, Stage II, 0.34 g, 5.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 40 mL), and the insoluble matter was removed by celite filtration. The filtrate was cooled to −35° C. to perform recrystallization; thus, $Co_2(CN^tBu)_8$ was obtained (13.9 mg, yield: 4%).

[Example 9] Synthesis of Cobalt Isocyanide Complex $Co_2(CN^tBu)_8$ Using Cobalt Iodide and $NaK_2$ Silica Gel (Stage I)

Cobalt iodide (0.31 g, 1.0 mmol), THF (15 mL), t-butyl isocyanide (0.33 g, 4.0 mmol), and $NaK_2$ silica gel (manufactured by Aldrich Corporation, Stage I, 0.41 g, 5.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 40 mL), and the insoluble matter was removed by celite filtration. The filtrate was cooled to −35° C. to perform recrystallization; thus, $Co_2(CN^tBu)_8$ was obtained (120 mg, yield: 31%).

Figure 4:
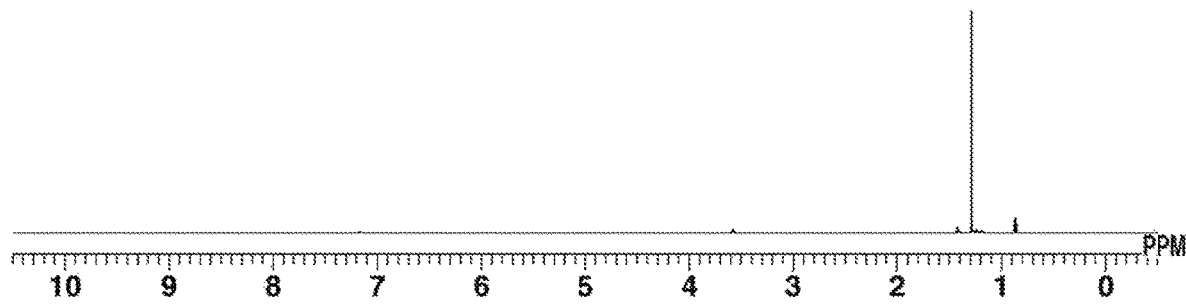
FIG. 4 is $^1$H-NMR spectrum diagram of $Fe(CN^tBu)_5$ obtained in Example 10.

[Example 10] Synthesis of Iron Isocyanide Complex $Fe(CN^tBu)_5$ Using Iron Bromide and $KC_8$ Iron bromide (22 mg, 0.10 mmol), THF (3 mL), t-butyl isocyanide (42 mg, 0.50 mmol), and $KC_8$ (manufactured by Strem Chemicals, Inc., 27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Fe(CN^tBu)_5$ was obtained (30 mg, yield: 63%). $^1$H-NMR spectrum of the resulting complex is shown in FIG. 4.
$^1$H-NMR (600 MHz, $C_6D_6$) δ: 1.29 (s, 45H).
IR (ATR): ν=2119, 2000, 1943, 1826 (CN) $cm^{-1}$

Figure 5:
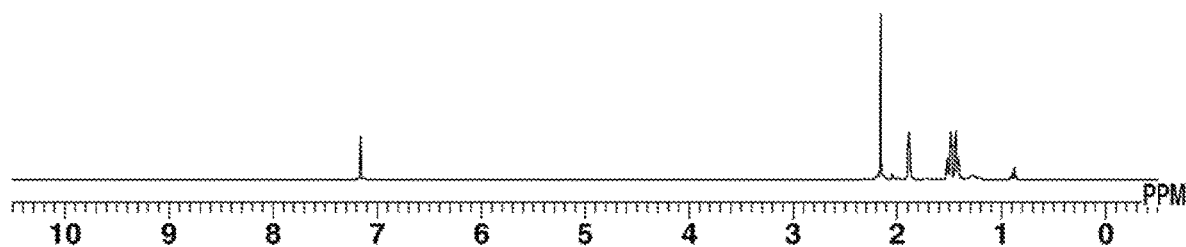
FIG. 5 is $^1$H-NMR spectrum diagram of $Fe(CNAd)_5$ obtained in Example 11.

[Example 11] Synthesis of Iron Isocyanide Complex $Fe(CNAd)_5$ Using Iron Bromide and $KC_8$ Iron bromide (216 mg, 1.0 mmol), THF (20 mL), adamantyl isocyanide (806 mg, 5.0 mmol), and $KC_8$ (manufactured by Strem Chemicals, Inc., 270 mg, 2.0 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in benzene (approximately 5 mL), and the insoluble matter was removed by celite filtration. Pentane was added to the filtrate, and then cooling was performed to −35° C. to perform recrystallization; thus, $Fe(CNAd)_5$ was obtained (601 mg, yield: 70%). $^1$H-NMR spectrum of the resulting complex is shown in FIG. 5.
$^1$H-NMR (396 MHz, $C_6D_6$) δ:
2.15 (s, 30H), 1.88 (s, 15H), 1.50 (d, J=11.5, 15H), 1.42 (d, J=11.5, 15H).
IR (ATR): ν=2106 (CN) $cm^{-1}$

Figure 6:
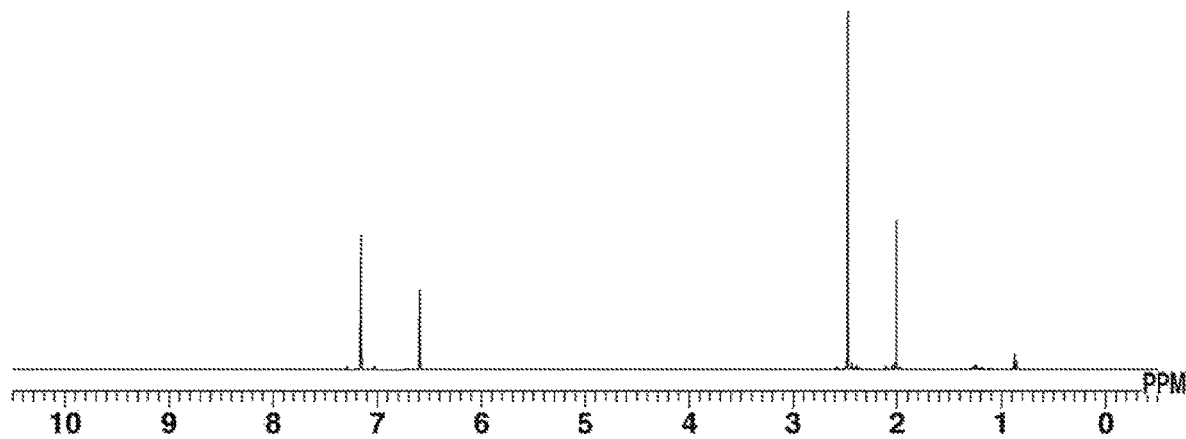
FIG. 6 is $^1$H-NMR spectrum diagram of $Fe(CNMes)_5$ obtained in Example 12.

[Example 12] Synthesis of Iron Isocyanide Complex $Fe(CNMes)_5$ Using Iron Bromide and $KC_8$ Iron bromide (22 mg, 0.10 mmol), THF (3 mL), mesityl isocyanide (73 mg, 0.50 mmol), and $KC_8$ (manufactured by Strem Chemicals, Inc., 27 mg, 0.20 mmol) were added in this order to a reactor, and stirring was performed at 25° C. for 12 hours. After that, the reaction solution was subjected to celite filtration, and the solvent of the filtrate was distilled under reduced pressure. The resulting dried substance was dissolved in toluene (approximately 3 mL), and the insoluble matter was removed by celite filtration. Pentane (approximately 3 mL) was slowly added from above the filtrate to perform recrystallization; thus, $Fe(CNMes)_5$ was obtained (18 mg, yield: 23%). $^1$H-NMR spectrum of the resulting complex is shown in FIG. 6.
$^1$H-NMR (600 MHz, $C_6D_6$) δ: 6.60 (s, 10H), 2.48 (s, 30H), 2.05 (s, 15H).
IR (ATR): ν=1971, 1940 (CN) $cm^{-1}$

Figure 7:
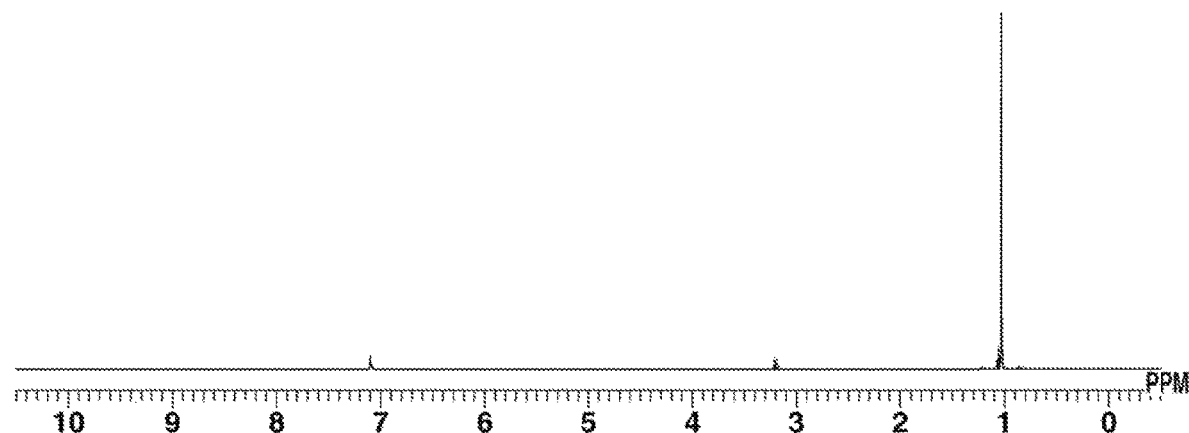
FIG. 7 is $^1$H-NMR spectrum diagram of $Ni(CN^tBu)_4$ obtained in Example 13.

[Example 13] Synthesis of Nickel Isocyanide Complex $Ni(CN^tBu)_4$ Using Nickel Bromide (Dimethoxyethane Adduct) and $KC_8$ Nickel bromide (a dimethoxyethane adduct) (31 mg, 0.1 mmol), THF (3 mL), t-butyl isocyanide (0.33 g, 0.4 mmol), and $KC_8$ (270 mg, 2.0 mmol) were added in this order to a reactor, and stirring was performed at room temperature for 30 minutes. After that, the reaction solution was subjected to celite filtration, and the solvent of the filtrate was distilled under reduced pressure. The resulting dried substance was dissolved in benzene (approximately 5 mL), and the insoluble matter was removed by celite filtration. Ether was added to the filtrate, and then cooling was performed to −35° C. to perform recrystallization; thus, $Ni(CN^tBu)_4$ was obtained (21 mg, yield: 54%). $^1$H-NMR spectrum of the resulting complex is shown in FIG. 7.
$^1$H-NMR (396 MHz, $C_6D_6$) δ: 1.09 (s, 36H).
IR (ATR): ν=2002 (CN) $cm^{-1}$

Figure 8:
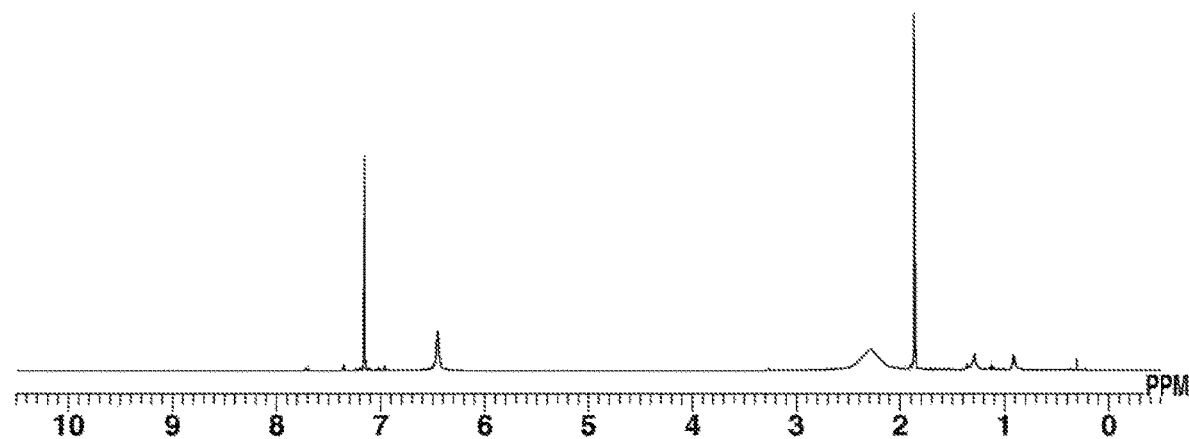
FIG. 8 is $^1$H-NMR spectrum diagram of $Pd_3(CNAd)_6$ obtained in Example 14.

[Example 14] Synthesis of Palladium Isocyanide Complex $Pd_3(CNMes)_6$ Using Palladium Chloride and $KC_8$ Palladium chloride (18 mg, 0.10 mmol), THF (3 mL), and mesityl isocyanide (29 mg, 0.20 mmol) were added to a reactor, and stirring was performed at 60° C. for 1 hour. Next, $KC_8$ (27 mg, 0.20 mmol) was added, and stirring was performed at room temperature for 30 minutes. After that, the reaction solution was subjected to celite filtration, and the solvent of the filtrate was distilled under reduced pressure. The resulting dried substance was cleaned with ether (approximately 2 mL) twice; thus, $Pd_3(CNMes)_6$ was obtained (25 mg, yield: 63%). $^1$H-NMR spectrum of the complex is shown in FIG. 8.

$^1$H-NMR (600 MHz, $C_6D_6$) δ: 6.45 (br, 10H), 2.29 (br, 30H), 1.87 (s, 15H).

IR (ATR): ν=2089, 1979, 1755 (CN) cm$^{-1}$

Figure 9:
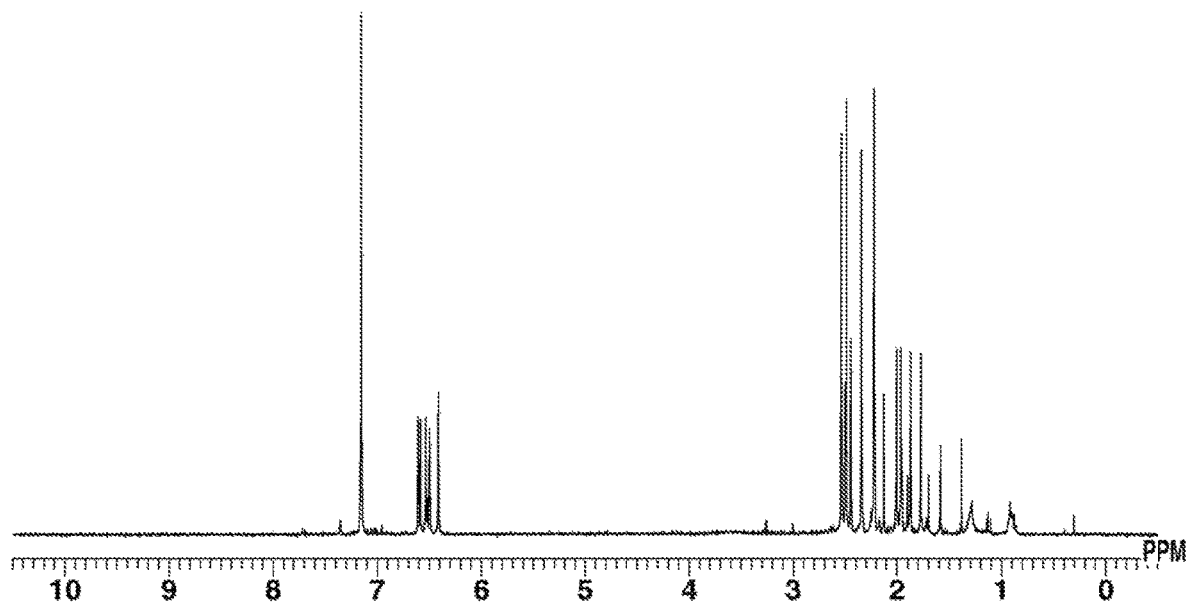
FIG. 9 is $^1$H-NMR spectrum diagram of a Pt-isocyanide complex obtained in Example 15.

[Example 15] Synthesis of Pt-isocyanide Complex Using Platinum Chloride and $KC_8$ Platinum chloride (27 mg, 0.10 mmol), THF (3 mL), and mesityl isocyanide (29 mg, 0.20 mmol) were added to a reactor, and stirring was performed at room temperature for 1 hour. Next, $KC_8$ (27 mg, 0.20 mmol) was added, and stirring was performed at room temperature for 30 minutes. After that, the reaction solution was subjected to celite filtration, and the solvent of the filtrate was distilled under reduced pressure. The resulting dried substance was dissolved in toluene (approximately 5 mL), and the insoluble matter was removed by celite filtration. Next, the solvent of the filtrate was distilled under reduced pressure, the resulting dried substance was dissolved in diethyl ether (approximately 1 mL), and the insoluble matter was removed by celite filtration again. The filtrate was cooled at −30° C. to perform recrystallization; thus, a Pt-isocyanide complex was obtained (7.7 mg, yield: 16%). $^1$H-NMR spectrum of the resulting complex is shown in FIG. 9.

IR (ATR): ν=2087, 1649, 1603 (CN) cm$^{-1}$

Figure 10:
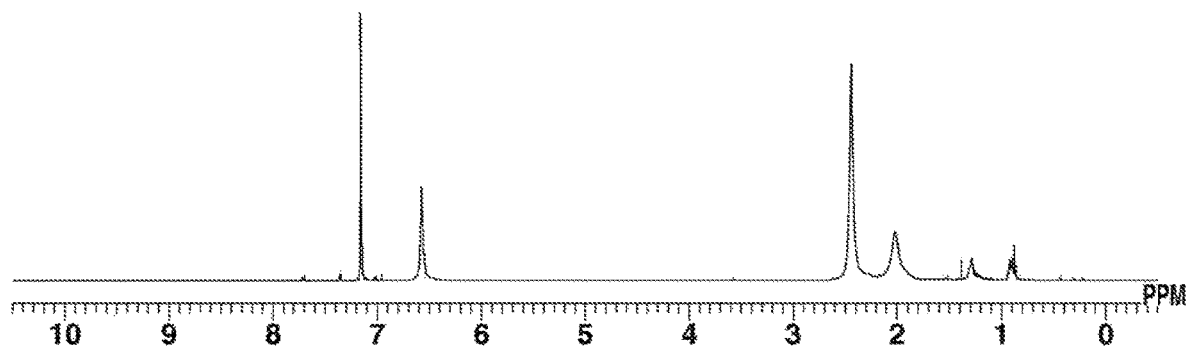
FIG. 10 is $^1$H-NMR spectrum diagram of $Rh_2(CNMes)_8$ obtained in Example 16.

[Example 16] Synthesis of Rhodium Isocyanide Complex $Rh_2(CNMes)_8$ Using chloro(1,5-cyclooctadiene)rhodium(I) dimers and $KC_8$ Chloro(1,5-cyclooctadiene)rhodium(I) dimers (25 mg, 0.05 mmol), mesityl isocyanide (58 mg, 0.40 mmol), THF (3 mL), and $KC_8$ (manufactured by Strem Chemicals, Inc., 14 mg, 0.10 mmol) were added in this order to a reactor, and stirring was performed at 25° C. for 1 hour. After that, the reaction solution was subjected to celite filtration, and the solvent of the filtrate was distilled under reduced pressure. The resulting dried substance was dissolved in benzene (approximately 3 mL), and pentane (approximately 10 mL) was added from above the filtrate to perform reprecipitation; thus, a rhodium isocyanide complex of $Rh_2(CNMes)_8$ was obtained (11 mg, yield: 16%). $^1$H-NMR spectrum of the resulting complex is shown in FIG. 10.

$^1$H-NMR (396 MHz, $C_6D_6$) δ: 6.57 (br, 16H), 2.44 (br, 48H), 2.01 (br, 24H).

IR (ATR): ν=1645, 1601 (CN (bridge)), 2051 (CN (terminal)) cm$^{-1}$

[Example 17] Synthesis of Cobalt Isocyanide Complex $Co_2(CN^tBu)_8$ Using bis(2,4-pentanedionato) Cobalt (II) and $KC_8$ Bis (2,4-pentanedionato) cobalt (II) (26 mg, 0.10 mmol), THF (3 mL), t-butyl isocyanide (33 mg, 0.40 mmol), and $KC_8$ (manufactured by Strem Chemicals, Inc., 27 mg, 0.20 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Co_2(CN^tBu)_8$ was obtained (6 mg, 15%).

[Example 18] Synthesis of Cobalt Isocyanide Complex $Co_2(CN^tBu)_8$ Using Cobalt (II) Isopropoxide and $KC_8$ Cobalt (II) isopropoxide (18 mg, 0.10 mmol), THF (3 mL), t-butyl isocyanide (33 mg, 0.40 mmol), and $KC_8$ (manufactured by Strem Chemicals, Inc., 27 mg, 0.20 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Co_2(CN^tBu)_8$ was obtained (3 mg, 8%).

[Example 19] Synthesis of Iron Isocyanide Complex $Fe(CN^tBu)_5$ Using Iron (II) Trifluoromethanesulfonate and $KC_8$ Iron (II) trifluoromethanesulfonate (35 mg, 0.10 mmol), THF (3 mL), t-butyl isocyanide (42 mg, 0.50 mmol), and $KC_8$ (manufactured by Strem Chemicals, Inc., 27 mg, 0.20 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Fe(CN^tBu)_5$ was obtained (11 mg, 23%).

Figure 11:
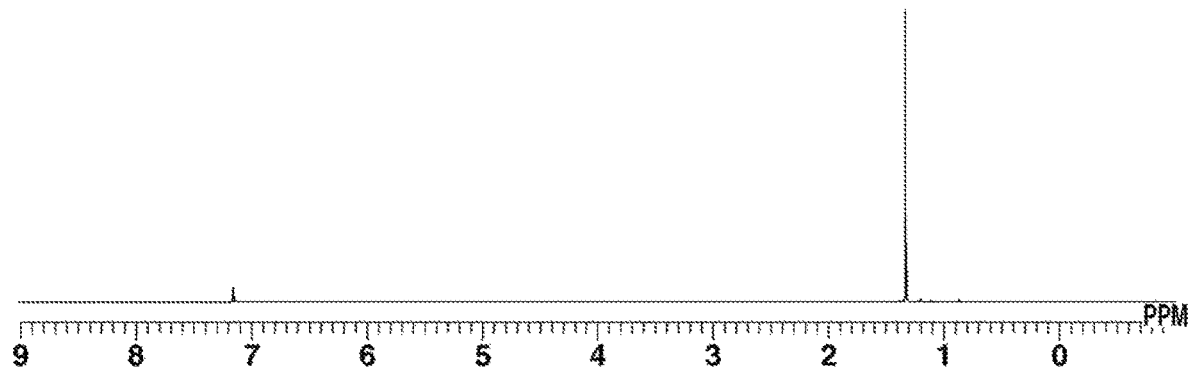
FIG. 11 is $^1$H-NMR spectrum diagram of $Mo(CN^tBu)_6$ obtained in Example 20.

[Example 20] Synthesis of Molybdenum Isocyanide Complex $Mo(CN^tBu)_6$ Using Molybdenum Acetate (II) Dimer and $KC_8$ Molybdenum acetate (II) dimer (21 mg, 0.05 mmol), THF (3 mL), t-butyl isocyanide (50 mg, 0.60 mmol), and $KC_8$ (manufactured by Strem Chemicals, Inc., 27 mg, 0.20 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, $Mo(CN^tBu)_6$ was obtained (3 mg, 2%). $^1$H-NMR spectrum of the resulting complex is shown in FIG. 11.

$^1$H-NMR (400 MHz, $C_6D_6$) δ: 1.33 (s, 54H).
IR (ATR): ν=2101, 1959 (CN) cm$^{-1}$

Figure 12:
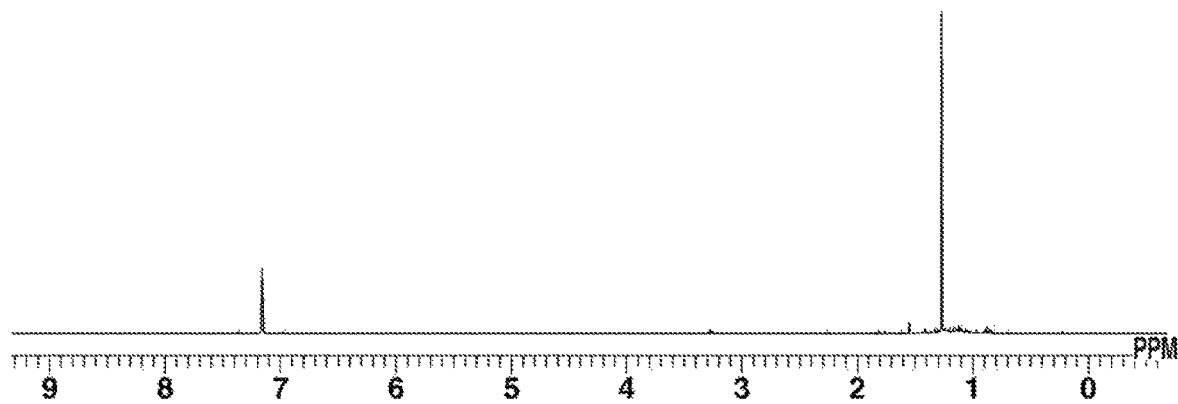
FIG. 12 is $^1$H-NMR spectrum diagram of $Ru(CN^tBu)_5$ obtained in Example 21.

[Example 21] Synthesis of Ruthenium Isocyanide Complex $Ru(CN^tBu)_5$ Using $Ru_2(OAc)_4Cl$ and $KC_8$ $Ru_2(OAc)_4Cl$ (22 mg, 0.05 mmol), THF (3 mL), t-butyl isocyanide (42 mg, 0.50 mmol), and $KC_8$ (manufactured by Strem Chemicals, Inc., 34 mg, 0.25 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, Ru(CN$^t$Bu)$_5$ was obtained (5 mg, 10%). $^1$H-NMR spectrum of the resulting complex is shown in FIG. 12.

$^1$H-NMR (400 MHz, C$_6$D$_6$) δ: 1.27 (s, 45H).
IR (ATR): ν=2070, 2034, 1815 (CN) cm$^{-1}$

Figure 13:
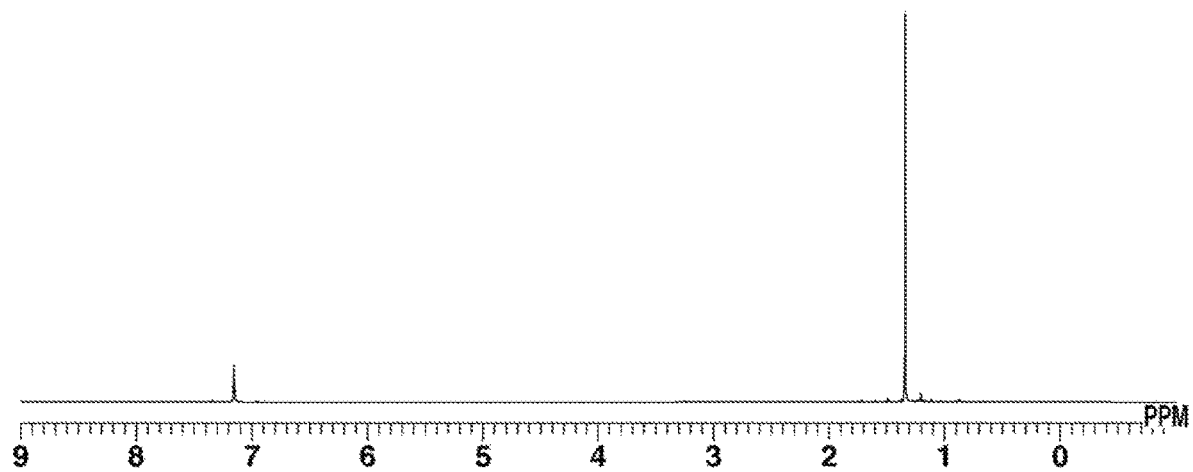
FIG. 13 is $^1$H-NMR spectrum diagram of $W(CN^tBu)_6$ obtained in Example 22.

[Example 22] Synthesis of Tungsten Chloride Complex W(CN$^t$Bu)$_6$ Using Tungsten Chloride (IV) and KC$_8$ Tungsten chloride (IV) (33 mg, 0.05 mmol), THF (3 mL), t-butyl isocyanide (50 mg, 0.60 mmol), and KC$_8$ (manufactured by Strem Chemicals, Inc., 54 mg, 0.50 mmol) were added in this order to a reactor, and stirring was performed at 25° C. for 3 hours. After that, the reaction solution was subjected to celite filtration, and the solvent of the filtrate was distilled under reduced pressure. The resulting dried substance was dissolved in pentane (approximately 4 mL), and the insoluble matter was removed by celite filtration. The filtrate was cooled to −35° C. to perform recrystallization; thus, W(CN$^t$Bu)$_6$ was obtained (10 mg, 15%). $^1$H-NMR spectrum of the resulting complex is shown in FIG. 13.

$^1$H-NMR (400 MHz, C$_6$D$_6$) δ: 1.34 (s, 54H).
IR (ATR): ν=1960 (CN) cm$^{-1}$

Figure 14:
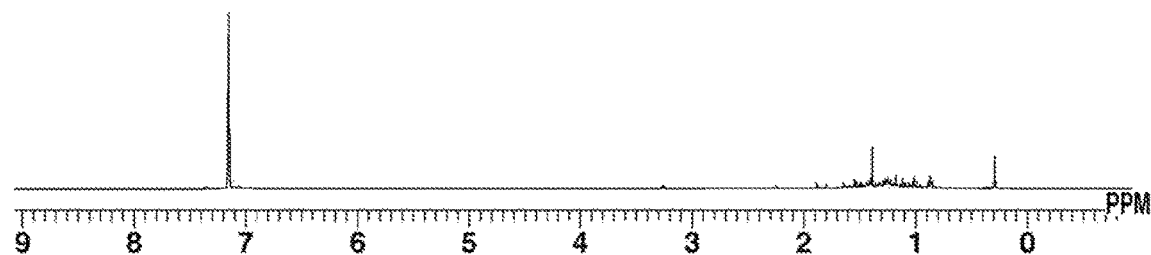
FIG. 14 is $^1$H-NMR spectrum diagram of a crude product containing $V(CN^tBu)_6$ obtained in Example 23.

[Example 23] Synthesis of Vanadium Isocyanide Complex V(CN$^t$Bu)$_6$ Using Vanadium(III) Bromide and KC$_8$ Vanadium(III) bromide (33 mg, 0.05 mmol), THF (3 mL), t-butyl isocyanide (50 mg, 0.60 mmol), and KC$_8$ (manufactured by Strem Chemicals, Inc., 41 mg, 0.30 mmol) were added in this order to a reactor, and stirring was performed at 25° C. for 3 hours. After that, the reaction solution was subjected to celite filtration, and the solvent of the filtrate was distilled under reduced pressure. The resulting dried substance was extracted by pentane (approximately 4 mL); thus, 9 mg of a crude product containing V(CN$^t$Bu)$_6$ was obtained. $^1$H-NMR spectrum of the resulting crude product is shown in FIG. 14.

$^1$H-NMR (400 MHz, C$_6$D$_6$) δ: 1.38 (s, 54H).

The invention claimed is:

1. A method for producing a transition metal-isocyanide complex represented by formula (2) below,
the method comprising reacting together a compound containing a transition metal selected from V, Cr, Mo, W, Fe, Ru, Co, Rh, Ni, Pd, and Pt, and an isocyanide compound represented by formula (1) below in the presence of an alkali metal supported by a solid substance insoluble in an organic solvent, $$(CN)_x—R^1 \quad (1)$$

wherein R$^1$ represents a monovalent to trivalent organic group that has 1 to 30 carbon atoms and is optionally substituted with a halogen atom and in which one or more atoms selected from oxygen, nitrogen, sulfur, and silicon are optionally interposed, and x represents an integer of 1 to 3, $$M^1{}_a(L)_b \quad (2)$$

wherein M$^1$ represents V, Cr, Mo, W, Fe, Ru, Co, Rh, Ni, Pd, or Pt with an oxidation number of zero, L represents an isocyanide compound represented by the formula (1), M$^1$ may be the same or different, and L may be the same or different, "a" represents an integer of 1 to 8, and "b" represents an integer of 2 to 12, and
wherein the solid substance insoluble in an organic solvent is at least one selected from a carbon material, a silicon compound, a metal oxide, and a polymer compound.

2. The method for producing a transition metal-isocyanide complex according to claim 1, wherein the compound containing a transition metal is at least one selected from a transition metal oxide, a transition metal acid or a salt thereof, and a halide salt, an oxyacid salt, a carboxylate, a sulfonate, an alkoxide salt, a β-diketonate, an amide salt, a tetrafluoroborate, or a hexafluorophosphate of the transition metal.

3. The method for producing a transition metal-isocyanide complex according to claim 1, wherein, in the formula (2), when a is 1, b is an integer of 2 to 6, when a is 2, b is an integer of 4 to 10, and when a is an integer of 3 to 8, b is an integer of 4 to 12.

4. The method for producing a transition metal-isocyanide complex according to claim 1, wherein, in the formula (1), x is 1.

5. The method for producing a transition metal-isocyanide complex according to claim 1, wherein, in the formula (2), M$^1$ is Cr, Mo, W, Fe, Ru, Co, Rh, Ni, Pd, or Pt.

6. The method for producing a transition metal-isocyanide complex according to claim 1, wherein, in the formula (2), when a is 1, b is an integer of 2 to 6, when a is 2, b is an integer of 4, or 8 to 10, and when a is an integer of 3 to 8, b is 4, 6, 7, 10, or 12.

7. The method for producing a transition metal-isocyanide complex according to claim 1, wherein M$^1$ in the formula (2) is Fe, Co, Rh, Ni, Pd, or Pt.

8. The method for producing a transition metal-isocyanide complex according to claim 1, wherein the compound containing a transition metal is a transition metal salt represented by formula (3) below, $$M^2X_c \quad (3)$$

wherein M$^2$ represents Cr, Mo, W, Fe, Ru, Co, Rh, Ni, Pd, or Pt, X represents a halogen atom or a group represented by formula (4) below each of which is possibly the same as or different from another one, and c represents an integer of 1 to 6, $$—OC(O)R^2 \quad (4)$$

wherein R$^2$ represents a monovalent organic group that has 1 to 30 carbon atoms and is optionally substituted with a halogen atom and in which one or more atoms selected from oxygen, nitrogen, sulfur, and silicon are optionally interposed.

9. The method for producing a transition metal-isocyanide complex according to claim 8, wherein, in the formula (3), M$^2$ is Fe, Co, Rh, Ni, Pd, or Pt.

10. The method for producing a transition metal-isocyanide complex according to claim 8 or 9, wherein R$^2$ in the formula (4) is a monovalent hydrocarbon group having 1 to 30 carbon atoms.

11. The method for producing a transition metal-isocyanide complex according to claim 10, wherein R$^2$ in the formula (4) is a methyl group.

12. The method for producing a transition metal-isocyanide complex according to claim 8, wherein X in the formula (3) is at least one selected from chlorine, bromine, and iodine.

13. The method for producing a transition metal-isocyanide complex according to claim 1, wherein $R^1$ in the formula (1) is a monovalent hydrocarbon group having 1 to 30 carbon atoms.

14. The method for producing a transition metal-isocyanide complex according to claim 1, wherein $R^1$ in the formula (1) is at least one hydrocarbon group selected from an alkyl group having 1 to 20 carbon atoms, a cycloalkyl group having 5 to 20 carbon atoms, an aryl group having 6 to 30 carbon atoms, and an alkylaryl group having 7 to 30 carbon atoms.

15. The method for producing a transition metal-isocyanide complex according to claim 14, wherein $R^1$ in the formula (1) is at least one hydrocarbon group selected from a t-butyl group, a 1-adamantyl group, a mesityl group, a phenyl group, a 2,6-dimethylphenyl group, and a 2,6-diisopropylphenyl group.

16. The method for producing a transition metal-isocyanide complex according to claim 1, wherein the solid substance insoluble in an organic solvent is at least one selected from graphite and silica gel.

17. The method for producing a transition metal-isocyanide complex according to claim 1, wherein the alkali metal is at least one selected from sodium, potassium, and sodium-potassium alloy.

* * * * *